(12) United States Patent
Nguyen-Xuan

(10) Patent No.: US 8,071,619 B2
(45) Date of Patent: Dec. 6, 2011

(54) INJECTABLE LIQUID FORMULATION OF PARACETAMOL

(76) Inventor: Tho Nguyen-Xuan, Vich (CH)

( * ) Notice: Subject to any disclaimer, the term of this patent is extended or adjusted under 35 U.S.C. 154(b) by 653 days.

(21) Appl. No.: 10/545,685

(22) PCT Filed: Feb. 16, 2004

(86) PCT No.: PCT/CH2004/000085
§ 371 (c)(1),
(2), (4) Date: Aug. 15, 2005

(87) PCT Pub. No.: WO2004/071502
PCT Pub. Date: Aug. 26, 2004

(65) Prior Publication Data
US 2006/0084703 A1 Apr. 20, 2006

(30) Foreign Application Priority Data
Feb. 14, 2003 (FR) ..................................... 03 01972

(51) Int. Cl.
C07C 211/00 (2006.01)
A01N 47/00 (2006.01)
A01N 31/08 (2006.01)
A61K 9/00 (2006.01)

(52) U.S. Cl. ........ 514/310; 424/400; 514/516; 514/731; 514/970; 564/7

(58) Field of Classification Search .................. 424/400; 514/516, 731, 970
See application file for complete search history.

(56) References Cited

U.S. PATENT DOCUMENTS

| | | | |
|---|---|---|---|
| 4,794,117 A | 12/1988 | Corbiere | |
| 6,028,222 A * | 2/2000 | Dietlin et al. | 564/4 |
| 6,992,218 B2 * | 1/2006 | Dietlin et al. | 564/4 |
| 2004/0054012 A1 | 3/2004 | Dietlin et al. | |
| 2004/0247627 A1 | 12/2004 | Nguyen-Xuan | |

FOREIGN PATENT DOCUMENTS

| | | |
|---|---|---|
| WO | 85/04106 A1 | 9/1985 |
| WO | 98/05314 A1 | 2/1998 |
| WO | 00/07588 A1 | 2/2000 |
| WO | 01/93830 A1 | 12/2001 |
| WO | WO 02/072080 A2 | 9/2002 |
| WO | WO 03/033026 A1 | 4/2003 |

OTHER PUBLICATIONS

Lambert et al., Organic Structural Spectroscopy. Upper Saddle River, NJ: Prentice-Hall, Inc., 1998.*

D. W. Potter et al.; "Identification of Acetaminophen Polymerization Products Catalyzed by Horseradish Peroxidase", The Journal of Biological Chemistry, vol. 260, No. 22, Oct. 5, 1985, pp. 12174-12180. (Cited in the int'l. search report).

R. P. Mason et al.; "Free Radicals of Acetaminophen: Their Subsequent Reactions and Toxicological Significance", Federation Proceedings, vol. 45, No. 10, Sep. 1986, pp. 2493-2499. (Cited in the int'l. search report).

William Clegg et al.; "An Oxidatively Coupled Dimer of Paracetamol", Acta Crystallographica, Secion C., Crystal Structure Communications, 1998, C54 (12), pp. 1881-1882. (Cited in the int'l. search report).

Roberto Andreozzi et al., Paracetamol oxidation from aqueous solutions by means of ozonation and $H_2O_2$/UV system, Water Research 37 (2003) 993-1004, Elsevier Science Ltd.

Potter et al., "Reactions of N-Acetyl-p-benzoquinone Imine with Reduced Glutathione, Acetaminophen, and NADPH," Molecular Pharmacology 30:33-41 (1986) (in English, cited in opposition to counterpart EP Pat. No. 1592414B1 (EP Appl. No. 04711333)).

Vilchez et al., "Spectrofluorimetric Determination of Paracetamol in Pharmaceuticals and Biological Fluids," J. Parm. Biomed. Anal., 13 :119-1125 (1995) (in English, cited in opposition to counterpart EP Pat. No. 1592414B1 (EP Appl. No. 04711333)).

"Dissociation Constants of Inorganic Acids in Aqueous Solutions," in Handbook of Chemistry and Physics, 65th Ed., CRC Press, Boca Raton, FL, p. D167 (1984) (in English, cited in opposition to counterpart EP Pat. No. 1592414B1 (EP Appl. No. 04711333)).

"Acetaminophen," in the Merck Index, 12th Ed., Merck & Co., Inc., Whitehouse Station, NJ, p. 47 (1996) (in English, cited in opposition to counterpart EP Pat. No. 1592414B1 (Ep Appl. No. 04711333)).

Fairbrother, Analytical Processes of Drug Substances, 3:1-109 (1974) (in English, cited in opposition to counterpart EP Pat. No. 1592414B1 (EP Appl. No. 04711333)).

Koshy et al., "Stability of Aqueous Solutions of N-Acetyl-p-Aminophenol," J. Of Pharmaceutical Sciences, 50 (2):113-118 (1961) (in English, cited in opposition to counterpart EP Pat. No. 1592414B1 (EP Appl. No. 04711333)).

"Protonic Equilibrium," in Mahler et al., Biological Chemistry, 2nd Ed. 1971, Harper & Row, New York, NY, pp. 13-15 (1971) (in English, cited in opposition to counterpart EP Pat. No. 1592414B1 (EP Appl. No. 04711333)).

(Continued)

*Primary Examiner* — Patricia A Duffy
*Assistant Examiner* — Chris E Simmons
(74) *Attorney, Agent, or Firm* — Westerman, Hattori, Daniels & Adrian, LLP

(57) ABSTRACT

The invention relates to a novel injectable liquid formulation of paracetamol, comprising an aqueous solvent, a buffer agent with a pKa between 4.5 and 6.5, an isotonic agent and the dimer of paracetamol of formula (I), a method for preparation of said formulation and the use of said dimer for the stabilisation of a liquid paracetamol pharmaceutical formulation.

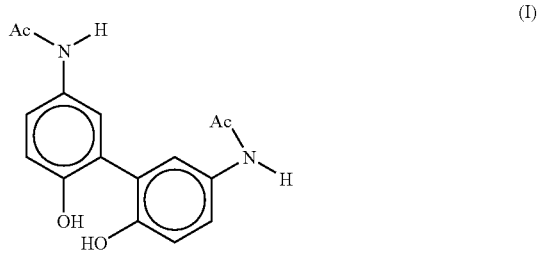

(I)

20 Claims, No Drawings

OTHER PUBLICATIONS

Buffer capacity, inonic strength, and tables of pKa, pp. 8-9, http://analytical.biochem.purdue.edu/~courses/undrgrad/221/wwwboard/handouts/index.html (downloaded Jan. 18, 2011) (in English, cited in opposition to counterpart EP Pat. No. 1592414B1 (EP Appl. No. 04711333)).

"General Preparative Procedures," in Methods in Enzymology, vol. I, Academic Press Inc., New York, NY, pp. 138-146 (1955) (in English, cited in opposition to counterpart EP Pat. No. 1592414B1 (EP Appl. No. 04711333)).

Swedish SmPC Perfalgan, http://www.lakemedelsverket.se/SPC_PIL/Pdf/humspc/Perfalgan%20solution%20for%20infusion@20.doc (downloaded Jan. 19, 2011) (no English translation—corresponds to UK SPC Perfalgan (Non Pat Lit #16), cited in opposition to counterpart EP Pat. No. 1592414B1 (EP Appl. No. 04711333) (alleged evidence of approval date of Perfalgan in Sweden on Feb. 8, 2002).

Nematollahi et al., "Electrochemical Oxidation of Acetaminophen in Aqueous Solutions: Kinetic Evaluation of Hydrolysis, Hydroxylation and Dimerization Processes," Electrochimica Acta, 54:7407-7415 (2009) (in English, cited in opposition to counterpart EP Pat. No. 1592414B1 (EP Appl. No. 04711333)).

Record from Newport database for injectable paracetamol (undated) (no English translation, cited in opposition.To counterpart EP Pat. No. 1592414B1 (EP Appl. No. 04711333) (alleged evidence of launch date of Perfalgan in Sweden on Feb. 28, 2002).

Excerpt from Chapter 84 "Sterilization," in Remington: Practice of, 19th Ed. 1995, Mack Publishing Co., Easton, Penn., p. 1463 (1995) (in English, cited in opposition to counterpart EP Pat. No. 1592414B1 (EP Appl. No. 04711333)).

Report of Analyses Carried Out by the Central Analysis Service of the University of the Basque Country (Spain) on 1592414B1 (EP Appl. No. 04711333)).

Fischer et al., "Free-Radical Metabolites of Acetaminophen and a Dimethylated Derivative," Environmental Health Perspectives, 64, 127-137 (1985) (in English, cited in opposition to counterpart EP Pat. No. 1592414B1 (EP Appl. No. 04711333)).

UK SPC Perfalgan, http://emc.medicines.org.uk/printfriendlydocumentaspx?documentid=142888,compa . . . (downloaded 16 Jul. 2009) (in English, corres to Swedish SmPC Perfalgan (Non Pat Lit #10) cited in opposition to counterpart EP Pat. No. 1592414B1 (EP Appl. No. 04711333)).

Koshy et al., Stability of Aqueous Solutions of N-Acetyl-p-aminophenol, J. Pharma. Sciences, pp. 113-118 (1960).

Alves et al. Density Functional Theory Study of Metabolic Derivatives of the Oxidation of Paracetamol, Int'l J. of Quantum Chemistry, vol. 106, pp. 2617-2623 (2006).

* cited by examiner

INJECTABLE LIQUID FORMULATION OF PARACETAMOL

The present invention relates to a novel injectable liquid pharmaceutical formulation of paracetamol containing a dimer of this active principle, to a process for preparing this formulation, and to the use of this dimer for stabilizing a liquid pharmaceutical formulation of paracetamol.

Paracetamol (INN of acetaminophen or N-(4-hydroxyphenyl)acetamide) is an analgesic and an antipyretic widely used in hospitals. It is desirable to have available stable liquid pharmaceutical formulations of this active principle for administration by injection, in particular for intravenous infusion.

It is known that paracetamol in aqueous solution is liable to undergo hydrolysis to form p-aminophenol, which is itself liable to degrade into quinoneimine (cf. for example J. E. Fairbrother, "Acetaminophen" in Analytical Profiles of Drug Substances, 1974, vol. 3, pp. 1-109). The rate of degradation of paracetamol increases with increasing temperature and light. This rate is minimal at a pH in the region of 6 (K. T. Koshy et al., 1961, J. Pharm. Sci. 50, pp. 116-118).

It is known practice to add a buffer and an antioxidant or free-radical scavenger to stabilize paracetamol in solution.

WO 02/072 080, for example, describes stable aqueous paracetamol solutions for infusion comprising a buffer of pH 5.5 to 6.5 and an antioxidant chosen from ascorbic acid and a derivative bearing a thiol function such as cysteine or acetylcysteine.

EP 0 916 347 discloses-paracetamol solutions based on a mixture of water and of alcoholic solvents comprising a buffer of pH 5.5 to 5.6 and metabisulfite as antioxidant.

The prior-art stabilized injectable solutions of paracetamol have the drawback of causing a potential irritant, allergenic and/or carcinogenic effect in certain patients, on account of the toxicity of the antioxidant they contain. Furthermore, their stability requires the removal of the oxygen and other oxidizing agents from the aqueous medium. These solutions therefore cannot be stored in plastic containers that are partially permeable to oxygen or that comprise traces of oxidizing residues.

The as yet unpublished patent application MI2001A002135 discloses stable injectable aqueous solutions of paracetamol obtained by mixing paracetamol with water, propylene glycol and a citrate buffer, heating the solution obtained to a temperature of between 70 and 130° C. and maintaining this solution at this temperature for at least 10 minutes. These solutions do not contain any toxic antioxidant, citric acid being a weak antioxidant widely used in the food industry.

D. W. Potter et al., 1985, J. Biol. Chem. 260, 22, pp. 12174-80 disclose the oxidation and polymerization of paracetamol in aqueous solution with hydrogen peroxide in the presence of horseradish peroxidase, isolation by semi-preparative HPLC and identification by mass spectrometry and NMR spectroscopy, of two dimers, two trimers and two tetramers of paracetamol. For a paracetamol concentration of greater than 0.2 mM, the dimer of formula (I) ("compound B") is largely predominant.

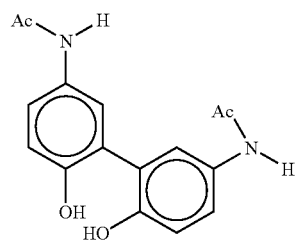

(I)

The problem or aim of the invention is that of finding a novel injectable liquid pharmaceutical formulation of paracetamol that is stable for a prolonged period without having the drawbacks mentioned above.

This problem is solved by the invention as defined by the attached claims.

The invention relates to an injectable liquid pharmaceutical formulation of paracetamol that contains paracetamol, an aqueous solvent, a buffer of pH between 4.5 and 6.5, an isotonic agent and paracetamol dimer of formula (I).

This paracetamol dimer, even in very small amount, appears to act as an antioxidant and makes it possible to dispense with the strong or toxic antioxidants described for the prior-art stabilized solutions of paracetamol.

The formulation of the invention has excellent stability at room temperature, and even at a temperature of the order of 40° C., and may be stored in a plastic container, in particular an infusion bag, for example a bag made of polypropylene, polyethylene, polyvinyl chloride or combinations of extruded polymers.

This paracetamol dimer may be replaced with another paracetamol polymerization product, for example a mixture of at least two oligomers of paracetamol chosen from the two dimers, the two trimers and the two tetramers of paracetamol described by D. W. Potter et al., 1985 in the reference cited hereinabove.

In general, this formulation contains at least 0.005% and preferably at least 0.05%, as a ratio of the surface area of the HPLC peaks with detection at 245 nm, of paracetamol dimer of formula (I).

The formulation of the invention may contain from 0.1 to 5.0 g/100 ml and preferably from 0.4 to 1.5 g/100 ml of paracetamol.

The aqueous solvent is water, of injectable grade, or a mixture of water and of one or more other water-miscible solvent(s), for example propylene glycol, polyethylene glycol, ethanol, and/or surfactants such as polysorbates or poloxamers. If the desired content of paracetamol in the solution exceeds 1.0 g/100 ml, the aqueous solvent will preferably be a mixture of water and of water-miscible solvent(s).

The formulation of the invention contains a buffer of pH between 4.5 and 6.5 and preferably between 5.0 and 6.2. This buffer will advantageously be chosen from citrate buffer, phosphate buffer, phosphate-citrate buffer, bicarbonate buffer, tartrate buffer and acetate buffer, preferably from citrate buffer, phosphate buffer and phosphate-citrate buffer, or a mixture of these buffers.

This formulation for injection contains an isotonic agent, intended to create an osmotic pressure in the region of that of physiological saline. This isotonic agent is generally chosen from sodium chloride and glucose.

The formulation of the invention is generally prepared by first mixing together paracetamol, injectable-grade water, optionally one or more other water-miscible solvent(s), and/or surfactants, buffer and isotonic agent, followed by heating the solution obtained, in bulk or prefilled in containers, at a temperature of at least 70° C. for at least 15 minutes. The aim of this heating is to remove any trace of nucleation that might trigger recrystallization of the paracetamol during the storage of the solution.

The invention also relates to a process for preparing the formulation defined above, which includes the mixing of paracetamol, water, optionally water-miscible solvent, and/or surfactants, buffer and isotonic agent, followed by heating of the solution obtained, in bulk or prefilled in containers, at a temperature of at least 70° C. for at least 15 minutes.

The dimer of formula (I) appears to form spontaneously but slowly during the storage of the solution obtained above at a sufficient temperature, for example 60° C.

To form the dimer of formula (I) in situ, it is practical to heat the solution at a temperature of between 100 and 130° C. and preferably between 110 and 125° C. for a period of at least 5 minutes.

The invention also relates to a process for preparing the formulation defined above, which includes the heating of the solution at a temperature of between 100 and 130° C. and preferably between 110 and 125° C. for a period of at least 5 minutes.

The invention also relates to a formulation as defined above that may be obtained via this process.

The invention also relates to the use of the dimer of formula (I) for stabilizing a liquid formulation of paracetamol. This dimer is generally manufactured in situ within the liquid formulation of paracetamol.

The invention is described in greater detail in the examples below, which are given as nonlimiting illustrations.

In these examples, the temperature is room temperature or is expressed in degrees Celsius, and the pressure is atmospheric pressure. The water, the propylene glycol and all the reagents used are of injectable grade.

Moreover, all the examples form an integral part of the invention, as does any characteristic of the description including the examples, which appears to be novel with respect to any prior art, in the form of a general characteristic rather than of a particular characteristic of the example.

EXAMPLE 1

Preparation of Liquid Pharmaceutical Formulations According to the Invention and Analysis of These Formulations by HPLC Formulations 001, 002, 003, 004, 005 and 006 were prepared by mixing together paracetamol, ultrapurified injectable-grade water, optionally (formulation 004) propylene glycol, buffer (phosphate buffer, citrate-phosphate buffer or citrate buffer) and isotonic agent (sodium chloride), heating at 70-90° C. for about 15 minutes to avoid the possibility of nucleation and consequent recrystallization of the paracetamol, and filling of glass bottles. These bottles were then sterilized for 15 minutes at 121° C.

The solutions were analyzed, before and after sterilization, by HPLC on a column of octylsilyl silica gel and a mobile phase obtained by mixing together a solution of disodium hydrogen phosphate, a solution of sodium dihydrogen phosphate and methanol R containing a solution of tetrabutylammonium R, and detection by spectrophotometry at 245 nm, according to the method recommended in the European Pharmacopoeia (European Pharmacopoeia 4.4, pp. 3503-4, 04/2003: 0049 Paracetamol).

A peak corresponding to an unknown substance (not accounted for by the European Pharmacopoeia) was detected. This substance was identified, by mass spectrometry coupled to liquid chromatography (LC-MS) and proton nuclear magnetic resonance (NMR) at 200 MHz, as being the paracetamol dimer of formula (I), which is identical to compound B described by D. W. Potter et al., 1985, J. Biol. Chem. 260, 22, pp. 12174-80.

The detection limit is about 0.005% for p-aminophenol and the dimer of formula (I). The difference between 100 and the paracetamol value measured is not significant and represents experimental uncertainty.

The compositions of these formulations and the HPLC analysis results are collated in table 1 below.

TABLE 1

| | Formulation | | | | | |
|---|---|---|---|---|---|---|
| | 001 | 002 | 003 | 004 | 005 | 006 |
| Paracetamol (g/100 ml) | 1.0 | 1.0 | 1.0 | 1.0 | 1.0 | 1.0 |
| Propylene glycol (g/100 ml) | — | — | — | 0.8 | — | — |
| Monosodium phosphate dihydrate (g/100 ml) | 0.1002 | 0.1071 | 0.0467 | — | — | — |
| Disodium phosphate dihydrate (g/100 ml) | 0.0785 | — | 0.0899 | 0.0877 | — | 0.091 |
| Citric acid monohydrate (g/100 ml) | — | — | — | 0.0499 | 0.033 | 0.045 |
| Sodium citrate dihydrate | — | — | — | — | 0.131 | — |
| Sodium chloride (g/100 ml) | 0.65 | 0.65 | 0.7 | 0.6 | 0.65 | 0.675 |
| Water for injection | to 100 ml | to 100 ml | to 100 ml | to 100 ml | to 100 ml | to 100 ml |
| pH | 5.7 | 4.7 | 6.9 | 5.2 | 5.3 | 5.4 |
| Osmolality (mosm/kg) | 284 | 290 | 307 | 290 | 287 | 296 |
| HPLC analysis | | | | | | |
| % dimer (before sterilization) * | nd | nd | nd | nd | nd | nd |
| % paracetamol (before sterilization) | 100.8 | 100.2 | 99.1 | 99.1 | 99.3 | 98.2 |
| % p-aminophenol (before sterilization) | nd | nd | nd | nd | nd | nd |
| % dimer (after sterilization) * | 0.07 | 0.02 | 0.12 | 0.04 | 0.05 | 0.08 |
| % paracetamol (after sterilization) | 100.7 | 100.7 | 98.5 | 98.6 | 99.1 | 98.6 |
| % p-aminophenol (after sterilization) | nd | nd | nd | nd | nd | nd |

* ratio of surface area of the peak for the dimer/surface area of the peak for paracetamol, in %
nd: not detected For these formulations, a content of the dimer of formula (I) of from 0.02 to 0.12 after sterilization was measured, this dimer not being detectable before the sterilization. The presence of p-aminophenol was not detected before or after sterilization.

EXAMPLE 2

Study of the Formation of the Dimer

1) Effect of Temperature and Time

The effect of the temperature on the formation of the dimer of formula (I) was studied on formulation 001 of example 1 after heating at 70-90° C. for 15 minutes and placing it in a glass bottle. This formulation was subjected to various storage temperatures and/or to various sterilization times, and analyzed by HPLC as described above in example 1.

The main results are collated in table 2 below.

TABLE 2

Effect of temperature and time on the formation of the dimer

| | Paracetamol (%) | p-Aminophenol (%) | Dimer (%) |
|---|---|---|---|
| Stored for 1 h at 70° C. (without sterilization) | 100.8 | not detected | not detected |
| Stored for 14 days at 60° C. (without sterilization) | 100.2 | not detected | 0.10 |
| Sterilized for 10 minutes at 121° C. | 99.9 | not detected | 0.09 |
| Sterilized for 20 minutes at 121° C. | 99.7 | not detected | 0.18 |
| Stored at 40° C. for 14 days, after sterilization for 15 minutes at 121° C. | 100.4 | not detected | 0.4 |

According to the above table, the dimer forms rapidly at 121° C., with a rate of formation proportional to the sterilization time, and slowly but in measurable amount at 60° C. for 14 days. The dimer is not detectable after one hour at 70° C.

p-Aminophenol is not detected under any of the conditions studied.

2) Effect of the pH

The values for the content of dimer of formula (I) given in table 1 of example 1 for formulations 001, 002 and 003 of compositions that are similar but with different pHs show that the formation of the dimer depends on the pH. The more basic the pH, the larger the amount of dimer formed. The generation of the radicals is probably facilitated by the formation of the phenoxides.

EXAMPLE 3

Stability Study

The stability was studied on formulation 001 of example 1 after heating at 70-90° C. for 15 minutes, put in glass bottles or polypropylene infusion containers, and sterilization at 121° C. for 15 minutes for the glass bottles and at 120° C. for 20 minutes for the polypropylene containers.

Table 3 below collates the results obtained by HPLC analysis as described in example 1 above.

TABLE 3

Stability of formulation 001

| | 50 ml glass bottle | | | 100 ml polypropylene container | | |
|---|---|---|---|---|---|---|
| | | 10 months | | | 10 months | |
| | Start | 25° C. | 40° C. | Start | 25° C. | 40° C. |
| Osmolality (mosm/kg) | 283 | 288 | 285 | 281 | 289 | 283 |
| Paracetamol content (%) | 100.3 | 100.7 | 99.1 | 100.3 | 100.4 | 99.4 |
| Dimer content (%) | 0.11 | 0.23 | 0.73 | 0.09 | 0.14 | 0.47 |
| p-Aminophenol content (%) | nd | nd | nd | nd | nd | nd |
| pH | 5.6 | 5.6 | 5.6 | 5.6 | 5.6 | 5.6 | nd: not detected

This table shows that the injectable liquid formulation according to the invention maintains the same paracetamol content after storage for 10 months at 25° C. or 40° C., with a slight increase in the dimer content, which is higher at 40° C. than at 25° C., and higher in the glass bottles than in the polypropylene containers.

The degradation of paracetamol in solution is often studied by measuring the absorbances at 500 nm according to the method described by J. E. Fairbrother "Acetaminophen", in Analytical Profiles of Drug Substances, 1974, vol. 3, pp. 1-109. Monitoring for three weeks, according to this method, of the absorbance firstly of formulation 001 and secondly of the commercial formulation Perfalgan® containing 1.0 g/100 ml of paracetamol and cysteine hydrochloride, obtained as described in WO 98/05314, shows that, at 60° C., paracetamol degrades at least ten times more quickly in the Perfalgan® formulation than in the formulation of the invention.

The invention claimed is:

1. A ready-to-use intravenous infusion solution of paracetamol, which contains paracetamol, an aqueous solvent, a buffer of pH between 4.5 and 6.5, an isotonic agent and a detectable amount of at least 0.005%, as a ratio of the surface area of peaks measured by HPLC with detection at 245 nm, of paracetamol dimer of formula (I) below:

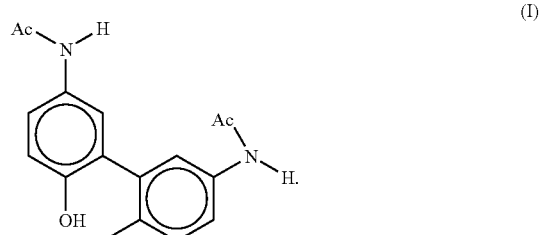

2. The formulation as claimed in claim 1, which contains from 0.1 to 5.0 g/100 ml of paracetamol.

3. The formulation as claimed in claim 1, which contains a buffer chosen from citrate buffer, phosphate buffer, phosphate-citrate buffer, bicarbonate buffer, tartrate buffer and acetate buffer, or a mixture of these buffers.

4. The formulation as claimed in claim 1, which is obtained via a process including heating of the solution in bulk or prefilled in containers at a temperature of between 100 and 130° C. for a period of at least 5 minutes.

5. A process for preparing a formulation as claimed in claim 1, comprising:
    mixing together paracetamol, water, optionally one or more water-miscible solvent(s), and/or surfactants, buffer and isotonic agent, followed by
    heating the solution obtained, in bulk or prefilled in containers, at a temperature of at least 70° C. for at least 15 minutes,
    so as to obtain the ready-to-use injectable liquid pharmaceutical formulation of paracetamol according to claim 1.

6. The process as claimed in claim 5, which includes heating the solution at a temperature of between 100 and 130° C. for a period of at least 5 minutes.

7. A glass container containing a formulation as claimed in claim 1.

8. Method of stabilizing a liquid formulation of paracetamol comprising:
    providing the dimer of formula (I) to a formulation containing paracetamol, an aqueous solvent, a buffer of pH between 4.5 and 6.5, and an isotonic agent,
    so as to obtain the ready-to-use injectable liquid pharmaceutical formulation of paracetamol according to claim 1.

9. The formulation as claimed in claim 1, which contains at least 0.05%, as a ratio of the surface area of the HPLC peaks with detection at 245 nm, of paracetamol dimer of formula (I).

10. The formulation as claimed in claim 1, which contains from 0.4 to 1.5 g/100 ml of paracetamol.

11. The formulation as claimed in claim 1, which contains a buffer chosen from citrate buffer, phosphate buffer and phosphate-citrate buffer.

12. The formulation as claimed in claim 1, which is obtained via a process including heating of the solution at a temperature of between 110 and 125° C. for a period of at least 5 minutes.

13. The formulation as claimed in claim 4, wherein the heating of the solution is performed in a polypropylene container.

14. The formulation as claimed in claim 11, wherein the heating of the solution is performed in a polypropylene container.

15. A plastic container containing a formulation as claimed in claim 1.

16. A polypropylene container containing a formulation as claimed in claim 1.

17. The process as claimed in claim 5, which includes heating the solution at a temperature of between 110 and 125° C. for a period of at least 5 minutes.

18. The process as claimed claim 5, wherein heating of the solution is performed in prefilled in containers.

19. The process as claimed in claim 18, wherein heating of the solution is performed in polypropylene containers.

20. The formulation as claimed in claim 1, wherein the composition does not further contain any additional antioxidant.

* * * * *